United States Patent [19]
Stanley et al.

[11] Patent Number: 5,991,948
[45] Date of Patent: Nov. 30, 1999

[54] FLUID SATURATED FOAM CONTAINER

[76] Inventors: Eric Stanley; Kirk Stanley, both of 130 W. Sycamore La., Louisville, Colo. 80027

[21] Appl. No.: 08/843,744

[22] Filed: Apr. 21, 1997

Related U.S. Application Data

[63] Continuation-in-part of application No. 08/331,183, Oct. 28, 1994, Pat. No. 5,632,051.

[51] Int. Cl.$^6$ .............................. A47C 27/08; A47C 27/18
[52] U.S. Cl. ................................. 5/709; 5/655.5; 5/682; 5/421; 5/925; 607/108
[58] Field of Search ........................... 5/709, 655.5, 682, 5/925, 644; 607/108–111

[56] References Cited

U.S. PATENT DOCUMENTS

| Re. 31,898 | 5/1985 | Suter | 5/709 |
|---|---|---|---|
| 3,574,873 | 4/1971 | Weinstein | 5/655.5 |
| 3,600,726 | 8/1971 | Williams | 5/682 |
| 3,872,552 | 3/1975 | Lea et al. | 5/709 |
| 4,370,768 | 2/1983 | Saloff | 5/682 |
| 4,459,714 | 7/1984 | Lin | 5/655.5 |
| 4,688,283 | 8/1987 | Jacobson et al. | 5/709 |
| 5,634,223 | 6/1997 | Obermaier | 5/925 |

FOREIGN PATENT DOCUMENTS 2697432  5/1994  France ...................................... 5/925

*Primary Examiner*—Alexander Grosz
*Attorney, Agent, or Firm*—Lee G. Meyer; Patton Boggs LLP

[57] ABSTRACT

A thermal regulating cushioning device includes a flexible, deformable outer membrane and a foam core contained therein having a dimension substantially coincident with the outer membrane. A liquid-like material is sealably contained within the outer membrane and saturates the foam core with the liquid-like material being at least partially circulatable through the foam core. The cooperation of the saturated foam core and the sealable flexible membrane provide a uniform, thermal regulating medium and structural support such that the cushioning device is readily, uniformly deformable when a load is applied thereto.

9 Claims, 5 Drawing Sheets

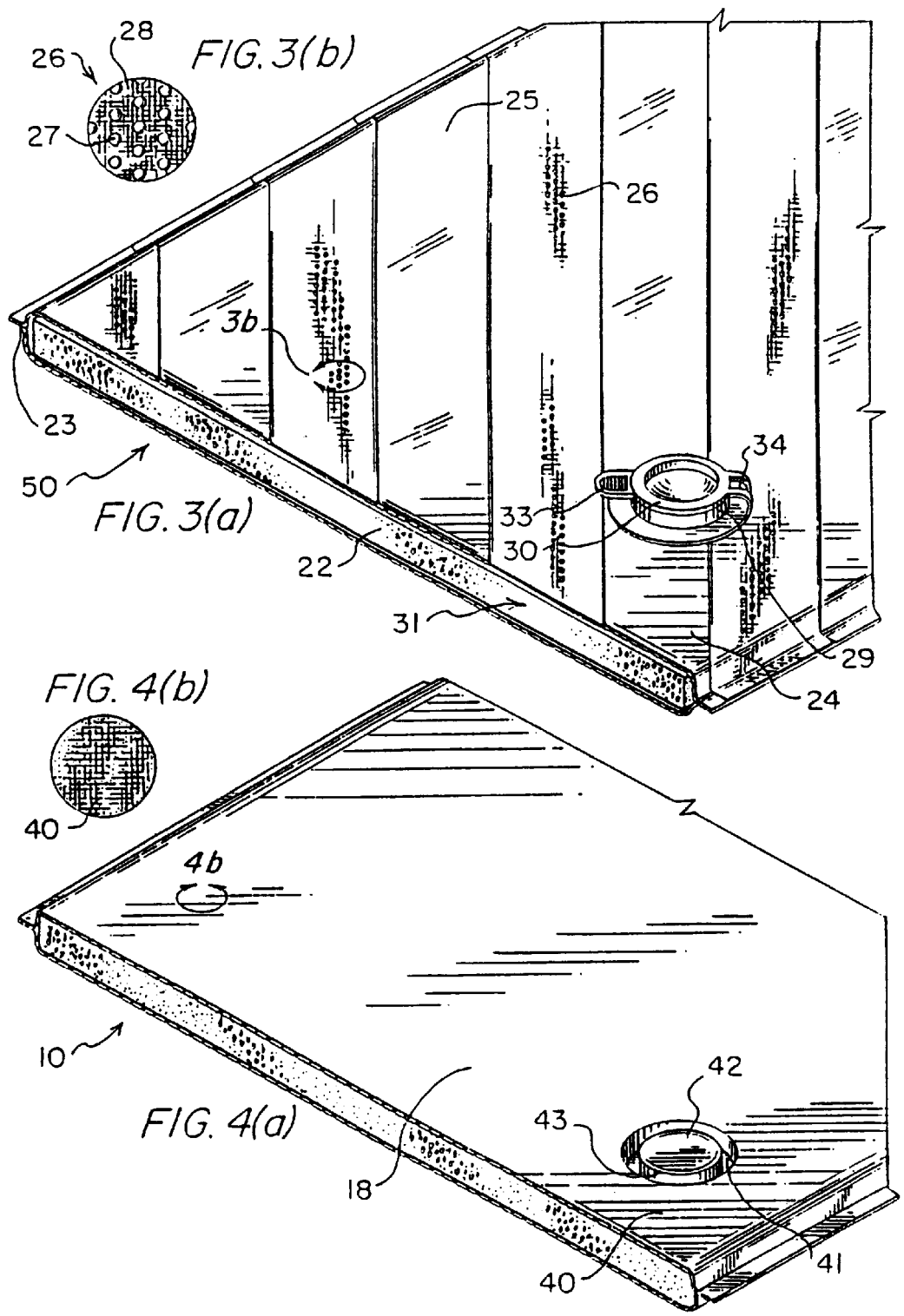

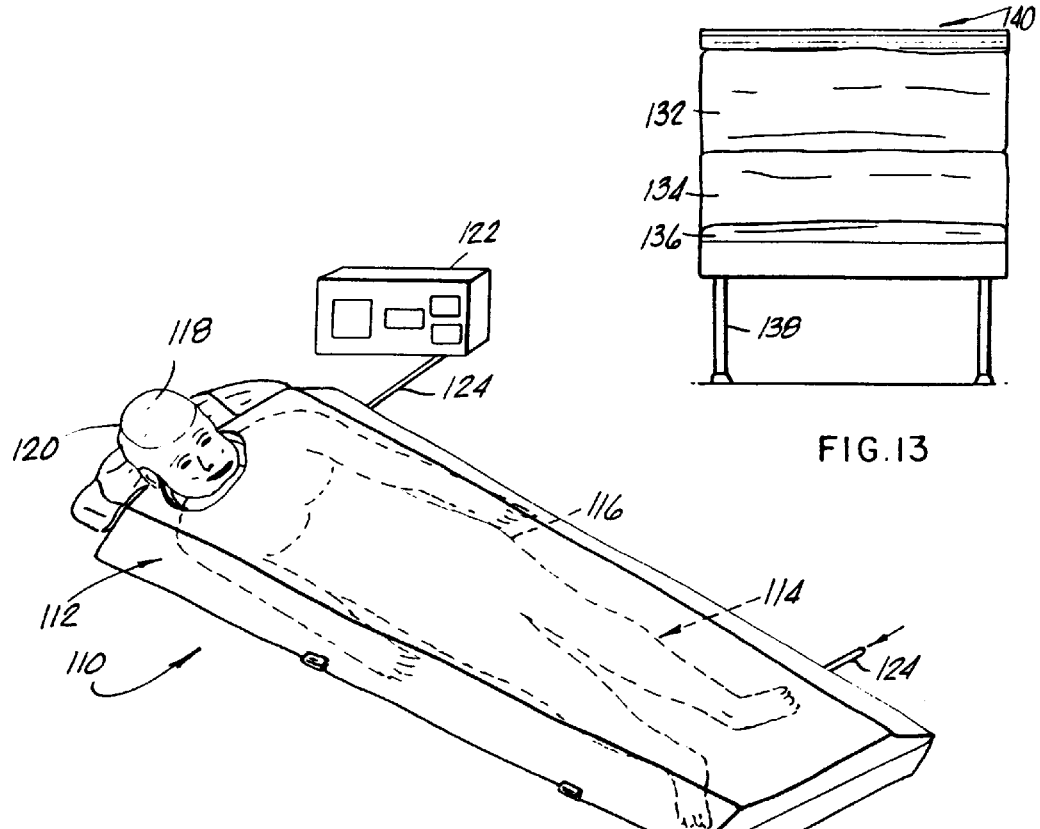
FIG. 13
FIG. 10
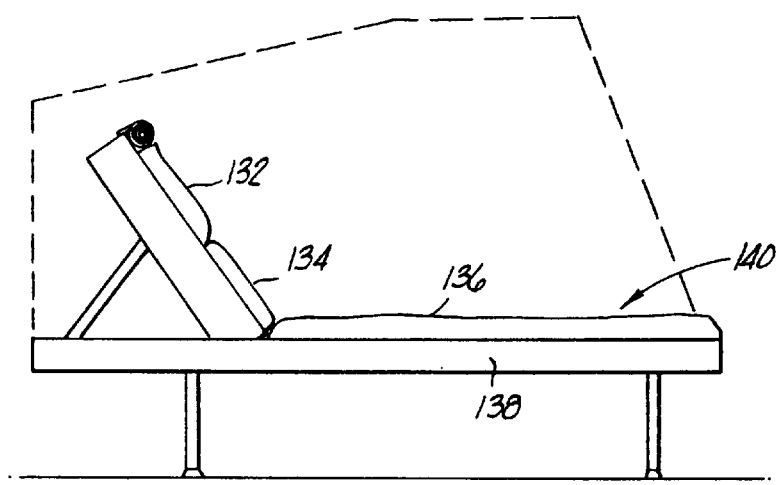
FIG. 12

FLUID SATURATED FOAM CONTAINER

The present application is a Continuation-in-Part of U.S. application Ser. No. 8/331,183 filed Oct. 28, 1994, for Fluid Cooling Container now U.S. Pat. No. 5,632,051. The parent application, which is incorporated by reference in its entirety, discloses a pillow insert comprising a liquid saturated, foam filled, container which slides between a pillow case and the top of a pillow to provide a constant cool spot for a pillow user and a pet cooling bed to make animals and family pets more comfortable.

BACKGROUND OF THE INVENTION

1. Field of the Invention

The instant invention relates to a liquid saturated, foam filled container as a device for simultaneously supporting and acting as a thermal regulator; and more specifically, to a liquid saturated foam filled cushioning support device for application in ,for example, the medical field, as well as for recreational use.

2. Description of Related Art

It has long been recognized that there are certain advantages to liquid containing devices, such as water beds, which support and/or act as thermal modulators and contain liquids, such as water, in a flexible or malleable container. The inherent drawbacks of such devices are that the liquid within the container moves freely without restriction and is required to bear the entire weight of a person or object placed thereon. Thus, such devices heretofore have relied upon increasing the pressure of the liquid within the container when an object is placed thereon in order to provide support. This makes them bulky and heavy. Further, when such devices are bent, or "wrapped", around an object, they tend to kink since the liquid is able to be totally displaced at the bend.

Many water bed or water pillow-type devices exist wherein fillers have been placed within the device in order to avoid sloshing or swishing of the liquid within the container or device. Prior art devices, including water filled devices, tend to kink or bend when a load is applied, for example, in wrapping such a device around one's arm, leg, etc. Even multi-chambered apparatuses are not satisfactory. The requirement that liquid pass freely in the device necessitates complicated valving devices between chambers. Still others employ valves, baffles, fillers, and the like to reduce wave motion and liquid displacement inherent in such liquid filled devices. Still other employ gels or deformable plastic type fillers.

Containers or continuous covers, such as sealable vinyl bags and the like, have also been filled with foams of various description in order to alleviate some of the problems inherent in the liquid filled devices. These foam-containing devices use the air filled foam structure as a support but do not provide the heat transferability of a liquid, nor the support afforded by a liquid containing device.

Specifically, Saloff et al. (U.S. Pat. No. 4,942,634) discloses a liquid displacement support system for dampening the wave motion in, for example, a conventional water bed, wherein at least two compartments have liquid communication, one with the other, through a plurality of orifices disposed in a membrane separating compartment to restrictively permit fluid migration from one chamber to another for the purpose of dampening the wave motion as between the chambers. Saloff discloses at least two compartments that are fluid-containing, with a valving structure such that the fluid migrates between valved compartments. Each of the compartments contains a saturated foam; however, eirculability of the fluid is not within the foam, but is between compartments with valving devices.

Sereboff (U.S. Pat. No. 5,195,199) discloses a cushion specifically designed to relieve load forces on the ischia spines of the user. Sereboff uses two, fluid medium, containing chambers disposed in relationship one to another. The fluid and/or the viscosity of the fluid in the two compartments can be varied to provide particular load distribution for the human body. The intermediate membrane is a closed cell, plastic-type composition impervious to liquid penetration, which sealably forms two separate cells or envelopes within the cushion. This configuration is specific to the application for relieving load forces on the ischia spines of the user.

Prete, Jr. (U.S. Pat. No. 3,864,766), discloses a relationship of air pressure in a gas filled, celled foam.

Haar, et. al. (U.S. Pat. No. 5,303,435) is a segmented air mattress that has an open celled material therein with individual valves controlling air flow into and out of the chambers. The valves operate individually to allow compression or expansion of the cells for storage and use.

U.S. Pat. No. 4,847,931 (1989) to Bard discloses a pillow with a thin water envelope contained in its bottom half. A dry compressible filler material lies between the pillow's top surface and the water envelope. U.S. Pat. No. 4,896,388 (1990) to Bard discloses an alternative embodiment of U.S. Pat. No. 4,847,931. The alternative embodiment uses a conventional pillow as the compressible filler material between the bottom water envelope and the top surface. Both suggest a standard foam filled pillow containing air, with an envelope portion below adapted to receive a fluid-like material.

U.S. Design Pat. No. 25,786 (1896) to Stoll discloses a water bag pillow having a large central hole and a tube at each of its four corners. The four tubes serve as both inlets and outlets and are closed by stoppers.

U.S. Pat. No. 4,887,326 to O'Brien et. al. discloses a crescent shaped neck pillow containing dry filling and pockets. The pockets receive gel packs which can be heated or cooled.

U.S. Pat. No. 5,231,720 (1993) to Benoff discloses a pillow having an internal air bag for adjustable firmness.

U.S. Pat. No. 4,908,893 to Smit discloses a beauty pillow with a concave area on its top surface to prevent pillow contact with delicate facial sldn. An optional water, air or gel filled bladder can be substituted for conventional pillow stuffing material.

It would be advantageous to have a lightweight device that afforded the structural support of foam and the heat transferability of a liquid, without the inherent problems of the unrestricted mobility of the liquid and the creation of pressure on the membrane required to support weight on the device.

SUMMARY OF THE INVENTION

It has now been unexpectedly discovered that by saturating the foam core of a foam filled, flexible, liquid impervious container or envelope with a liquid, the structural stability as well as the load bearing ability of the device can be enhanced while still allowing selected mobility of the liquid to provide enhanced thermal regulation, flexibility, mobility, and applications not available with prior art devices.

In accordance with the invention, there is provided a liquid saturated, foam filled flexible device having a flexible, liquid impervious outer membrane encapsuatinpg a foam filler of substantially the same dimensions as the membrane, wherein the foam filler is saturated with a liquid such that the liquid has at least partial mobility through the foam filler and the foam and the liquid cooperate within the confines of the outer membrane to provide the device with both flexibility and structure stability. In one aspect, the liquid saturated foam filled flexible container has application as a pillow insert the device is positioned between the pillow case and the pillow to provide support and heat dissipation to the head of the user. In another embodiment, the device provides a pad or "mattress" for a human or an animal which, when drained of liquid, is lightweight and compact and, when filled with liquid, has high support characteristics and provides cushioning for pressure contact points of the user. In yet another embodiment, the container can be "formed," such as in the case of a body cast or the like, to provide a heat dissipating cushioned barrier to transport and stabile burn victims or highly traumatized patients. In accordance with this embodiment, the surface of the device which comes in contact with the user is coated with a non-stick surface, to prevent adhesion of damaged skin to the surface of the device.

In the present invention, the liquid impervious, flexible container is substantially filled with a porous foam material which is saturated with a liquid. In one aspect, the container cools or heats a person by allowing convective heat exchange between a person's body, and the liquid in the container. This conducted heat is passively dissipated by the device to the surrounding environment. The liquid migrates freely through the foam, therefore, "hot spots" do not occur and temperature remains uniform throughout the container. In one embodiment, there is provided a thermal regulator to cool or heat the liquid, as well as providing circulation of the thermally regulated liquid within the container.

Further, the saturated foam reduces the water leakage in case of a puncture and prevents noise by preventing waves. The container can be used as a belt to provide constant temperature, sleeping, and resting conditions for humans, animals and family pets or as a mattress for camping, or the like. Use as a seat cushion or lounge chair liner are also within the scope of the present invention. A thermal regulating unit can be attached to regulate the temperature of the bed, if so desired.

In operation, the user brings at least a portion of her/her body into intimate contact with the device which, by action of the liquid saturated foam in cooperation with the outer membrane, supports the user and simultaneously provides thermal regulation.

Advantages of this invention will appear from the following description and appended claims, reference being had to the accompanying drawings forming a part of this specification wherein like reference characters designate corresponding parts in the several views.

BRIEF DESCRIPTION OF THE DRAWINGS

FIG. 3(a) is a top perspective view of the bottom side of an alternative embodiment of the liquid container pillow insert of the present invention.

FIG. 3(b) is a top plan view of the traction material which is fixed to the bottom side of the alternative embodiment of the liquid container pillow insert of the present/invention.

FIG. 4(a) is a top perspective view of the bottom side of the preferred embodiment of the liquid container pillow insert of the present invention.

FIG. 4(b) is a top plan view of the flocked vinyl traction material which is fixed to the bottom side of the preferred embodiment of the liquid container pillow insert of the present invention.

FIG. 10 is a top perspective view of a further alternative embodiment of the liquid container of the present invention being used as a substantially encapsulating thermal regulating bed with an external thermal regulating device connected thereto.

FIG. 12 is a side view of an additional further alternative embodiment of the liquid container of the present invention being used as a lounge chair liner.

FIG. 13 is a front view of the lounge chair liner embodiment of the liquid container of the present invention.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE DRAWINGS

Figure 1:
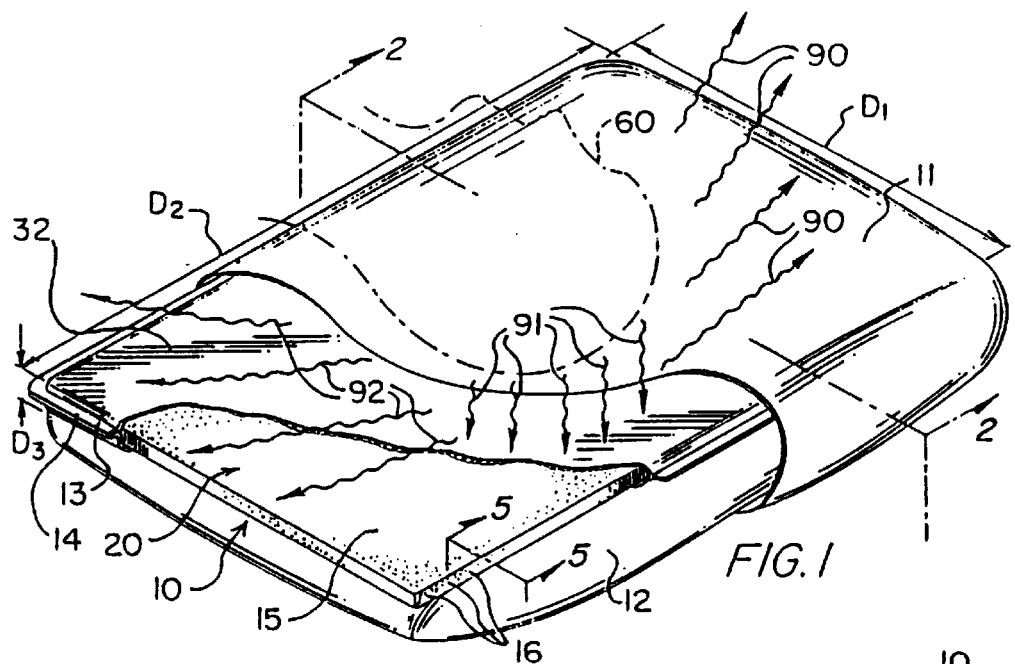
FIG. 1 is a top perspective view of a partial cut-away of the liquid saturated foam filled pillow insert of the present invention enclosed between a pillow and pillow case.

Referring first to FIG. 1 a top perspective view of a partial cut-away of the liquid container pillow insert 10 enclosed between a pillow 12 and pillow case 11 is shown. The pillow insert consists of a foam core 15 that is saturated with liquid 20 and enclosed in a container 13.

A liquid container pillow insert 10 has a foam core 15. The liquid impervious flexible container 13, for example vinyl, fits snugly around the foam core 15. The dimensions of the pillow insert 10 and the container are preferably substantially larger than a human head (60) and provide enough volume and surface area to dissipate the body heat transferred to the insert 10.

The container 13 consists of two layers of vinyl which have been sealed together along their perimeters by, for example, radio frequency or other means. Flexible vinyl sheets are available in thickness, for example, ranging from 2 mm to 100 mm. The preferred embodiment uses 8 mm thick vinyl sheets. The resulting radio frequency seal 14 is water tight and stronger than a heat seal. The top vinyl sheet 32 is, for example, noiseless, translucent and soft to the touch.

Figure 5:
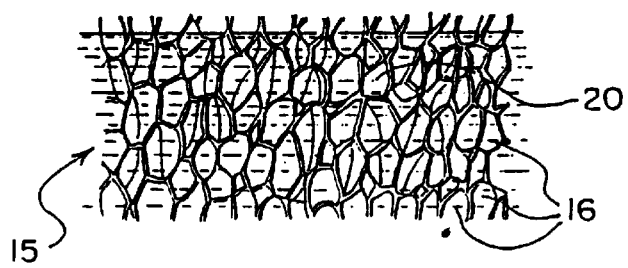
FIG. 5 is a cross-sectional view of the reticulated foam contained in the liquid container pillow insert of the present invention.

Referring next to FIG. 5, a cross-sectional view of the foam core 15 contained in the liquid contained pillow insert 10 is shown. The core 15 consists of foam composed of, for example, polyurethane which contains pores 16. The foam is preferably of an open pore structure to allow substantially free mobility of the liquid within the foam. The foam core 15 is saturated with a liquid 20. The foam can be processed with an acid treatment or sonic treatment to result in larger pore sizes and is available in, for example, pore densities ranging from ten pores per inch (PPI) to sixty PPI. The preferred embodiment of the pillow insert 10 has a foam core 15 with a pore density of about twenty PPI. At this pore density, a stable insert 10 retains essentially all of the liquid 20 in the foam core 15. This reduces both noise and the risk of leakage if the container 10 is punctured or torn. Noise is reduced because liquid 20 is retained in the foam core 15 and not free to audibly slosh or splash. Risk of leakage is reduced because liquid is retained in the foam and not as freely mobile to leak out of a puncture or a cut. Thus, the foam core 15 tends to not release the liquid 20 to result in leakage unless pressure is applied at or near a puncture or cut. Additionally, because all the liquid is evenly distributed throughout the core 15, the liquid 20 does not tend to pool in one spot. This allows the core 15 to act as a weight sink to stabilize the invention and prevent the invention from slipping out of place. The preferred liquid 20 used in insert 10 is water.

Figure 2:
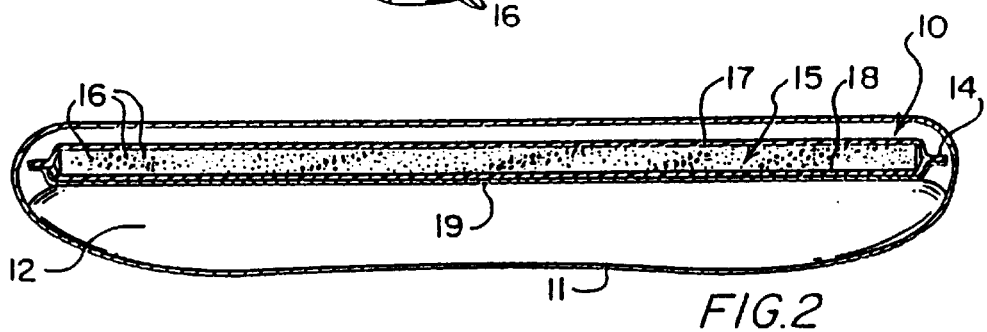
FIG. 2 is a front cross-sectional view of the liquid container pillow insert of the present invention enclosed between a pillow case and pillow.

Referring next to FIG. 2, a front cross-sectional view of the liquid container pillow insert 10 enclosed between a pillow 12 and a pillow case 11 is shown. The container 10 consists of a top vinyl sheet 17 and bottom vinyl sheet 18 which are radio frequency sealed 14 to enclose a reticulated foam insert 15. A backing 19 is fixed to the bottom vinyl sheet 18. The container 10 is placed on a conventional pillow with the backing 19 contacting the pillow 12 and the top vinyl sheet 17 facing up.

Referring again to FIG. 1, the only layer between the liquid container pillow insert 10 and a person's head 60, is the pillow case 11. This close contact allows a user's body heat to be absorbed by the insert (10) and conducted throughout the liquid 20 and finally passively transferred to the surrounding environment as indicated by arrows 91. The liquid 20 disperses body heat from the point where the head contacts the pillow and diffuses the heat throughout the liquid container pillow insert 10 as indicated by arrows 92.

The liquid temperature may initially be at room temperature which is lower than human body temperature and remains so for hours. A user may also adjust the initial temperature of the liquid 20 by filling the container 10 with a liquid 20 at the desired temperature or attaching, for example, a heating or cooling device as set forth in FIG. 9 in respect to a further embodiment. By dispersing a person's body heat throughout the liquid container pillow insert 10, the pillow surface remains uniformly cool providing a person with a constant cool surface to sleep on. The liquid container pillow insert 10 warms slightly from the body heat of the user during use. If the user desires an initial temperature lower than room temperature, the user can fill the container with cooler water. Heat transfer to the pillow insert 10 helps to enhance sleeping comfort by conducting heat away from a person's head 60.

A pillow case 11 fits securely around the insert 10 and a conventional pillow 12. The combination of the traction backing 19, the snug pillow case 11, and the weight of the insert 10, securely holds the container 10 flat against the pillow 12.

Referring next to FIG. 3(a) a top perspective view of the bottom side of an alternative embodiment of the liquid container pillow insert 50 is shown. The alternative embodiment of the container 50 consists of a foam core 22 which is saturated with liquid 31, preferably water, and snugly enclosed by vinyl container 24. The vinyl container 24 consists of two vinyl sheets fused together around their perimeters by a radio frequency seal 23.

In the alternative embodiment of the container 50, a simple liquid inlet 29 is attached to the bottom 25 of the vinyl bag 24. The inlet 29 is a funnel opening which is easily opened and closed by a pop cap 30 using a pull tab 33. The pop cap 30 is attached to the inlet by thin plastic strips 34 to prevent the loss of the pop cap 30. Strips of traction material 26 are attached to the bottom 25 of the vinyl bag 24 to help maintain the container 50 properly oriented flat against a pillow.

Referring next to FIG. 3(b) a top plan view of the traction material 26 which is fixed to the bottom side of the alternative embodiment of the pillow insert 50 is show, preferably a traction material such as JIFFY GRIP brand. JIFFY GRIP brand consists of cloth 28 studded with raised vinyl dots 27. The JIFFY GRIP brand traction material 26 contacts the top of a pillow and keeps the insert 50 from slipping out of position. Similar traction material with rubber dots is also available from other manufacturers. The JIFFY GRIP brand traction material combined with the weight of the insert 50 and the tension of the pillow case, keeps the insert 50 properly oriented on the pillow. Additionally, because the liquid 31 is uniformly distributed throughout the foam core 22, the liquid 31 does not pool. The container 50, therefore, acts as a weight sink and is not pulled out of orientation by pooled liquid 31.

Referring next to FIG. 4(a) a top perspective view of the bottom side of the preferred embodiment of the liquid container pillow insert 10 is shown. In the preferred embodiment, a recessed finger-well style valve 43 is inserted through the bottom vinyl sheet 18 of the container 10. The seal 41 between the valve 43 and the bottom vinyl sheet 18 is water tight. The valve 43 is one half to one inch in diameter and is sealed by a threaded screw cap 42. The cap 42 is unscrewed when liquid is added to or removed from the insert 10. The bottom sheet 18 also comprises a traction material 40.

Referring next to FIG. 4(b) a top plan view of the traction material 40 which is fixed to the bottom vinyl sheet 18 of the preferred pillow insert 10 is shown. The traction material 40 is composed of flocked vinyl. The traction material 40 contacts the top surface of a pillow 12 and prevents the container 10 from slipping out of position. The combination of the flocked vinyl 40, bottom sheet 18, the weight of the container 10, the lack of liquid 20 pooling, and the tension of the pillow case 11, keeps the container 10 in the proper orientation on the pillow 12.

Figure 6:
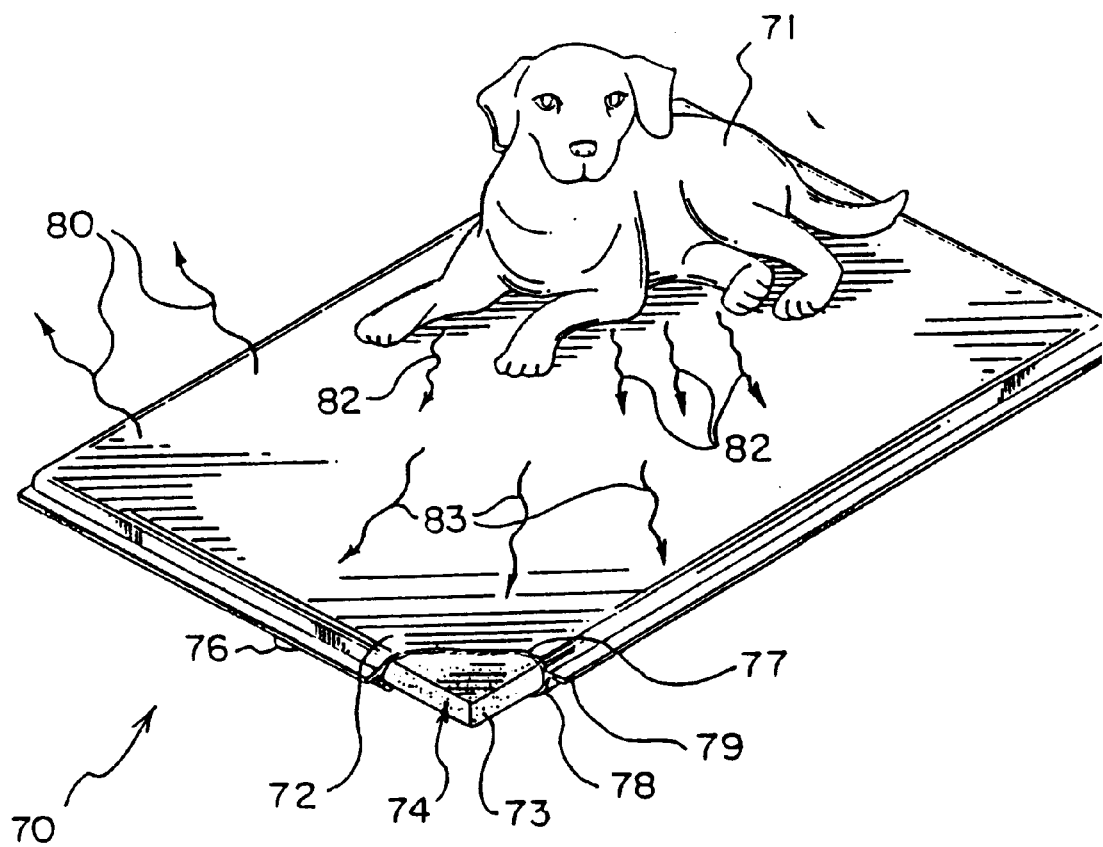
FIG. 6 is a top perspective view of a partial cut-away of an alternative embodiment of the liquid container of the present invention being used as a cooling pet bed.

Referring next to FIG. 6, a top perspective view of a partial cutaway of an alternative embodiment is illustrated. The pet bed 70 of the present invention is substantially similar to the container 10 and the container 50.

The pet bed 70 consists of a foam core 73 saturated with liquid 74 and snugly enclosed by a vinyl container 72. The vinyl container 72 is composed of an upper vinyl sheet 77 and a lower vinyl sheet 78 fused together to form a strong water tight seal 79. The flexible vinyl sheets are available in thicknesses that range from 2 millimeters to 100 millimeters. Vinyl sheets having a thickness of approximately 20 millimeters which are employed in the pet bed 70 help prevent an animal's claws from tearing or puncturing the pet bed 70. The pet bed 70 has a simple liquid inlet and outlet 76 attached in a water tight fashion to its vinyl sheet 78. The reticulated foam core 73 of the pet bed 70 is saturated with a liquid, preferably with water 74.

The pet bed 70 has a dimension substantially larger than the body size of the animal. The pet bed 70 is preferably twice the size of the pet's body size in order to provide enough volume and surface area to dissipate the animal's 71 body heat. Similar to pillow insert 10 shown in FIG. 1, the body heat of the animal 71 is absorbed by the saturated foam core 73 and conducted throughout the liquid 20, as indicated by arrows 82 and 83, a finally to the surrounding environment, as indicated by arrows 80.

Figure 7:
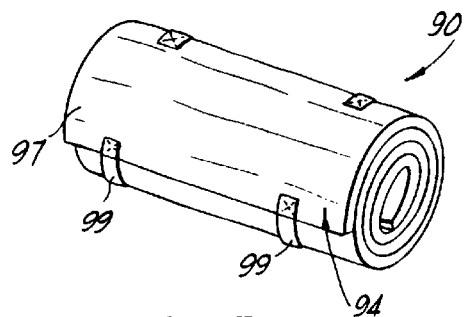
FIG. 7 is a perspective view of yet another alternative embodiment of the liquid container of the present invention for use as a bed liner, the bed liner being rolled for easy storage and carrying.
Figure 8:
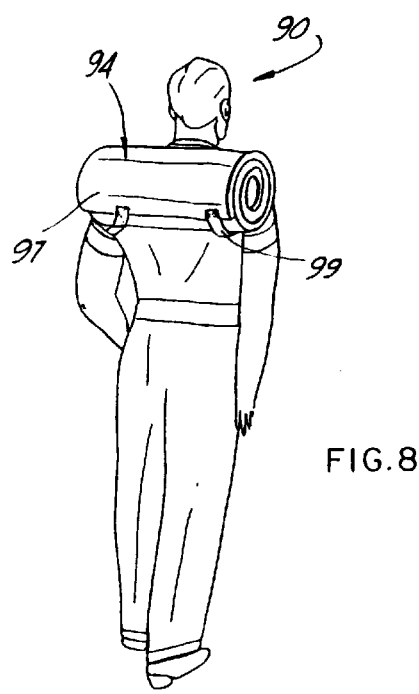
FIG. 8 is a perspective view of the bed liner embodiment of the liquid container of the present invention being carried on a person during transit.

Referring next to FIGS. 7 and 8, a perspective view of another embodiment 90 for use as a portable bed liner or pad is illustrated. The bed liner 90 of the present invention is substantially similar to the previously described container 10, container 50, and the pet bed 70.

As described in the pet bed 70, the bed liner 90 consists of a foam core (not shown). The foam core is saturated with liquid and snugly enclosed by a vinyl covering 94. The vinyl covering 94 preferably has an upper sheet (not shown) and a lower vinyl sheet 97 opposite the upper sheet with the upper and lower vinyl sheets being fused together with a strong water tight seal, for instance by use of radio frequency. The flexible vinyl sheets of the vinyl cover 94 are available in thicknesses that range from 2 millimeters to 100 millimeters. Vinyl sheets having a thickness of approximately 20 millimeters which are used in the bed liner 90 inhibit tearing or puncturing the liner 90 during transit, storage, and outdoor use. Although not illustrated in FIGS. 7 and 8, the liner 90, similar to the pet bed 70, has a simple liquid inlet and outlet for introduction and removal of liquid into and out of the liner 90. The liquid inlet and outlet is attached in a water tight fashion to the vinyl covering 94. In the bed liner 90, the foam core is saturated with water as the preferred liquid.

Preferably, the bed liner 90 has a dimension substantially larger than the body size of a human. Furthermore, the bed liner 90 is rollable into a smaller size and held together by straps 99 to provide easier storage and transportation of the bed liner 90 for use when camping and hiking, for example.

Figure 9:
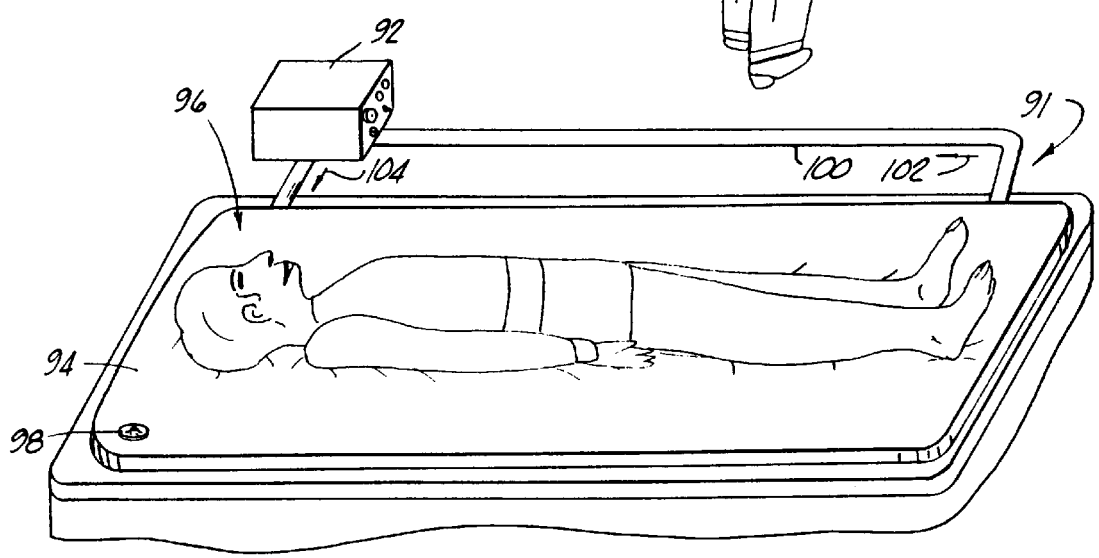
FIG. 9 is a top perspective view of still another alternative embodiment of the liquid container of the present invention being used as thermal regulating bed with an external thermal regulating device connected thereto.

Referring next to FIG. 9, a top perspective view of another embodiment of the present invention illustrates a human bed 91. This embodiment is ideally suited for use with the infirm, hospital patients, or others who are confined to their beds for extended periods of time. Often, when an individual must lie in bed in substantially the same position for great lengths of time, a standard foam mattress, waterbed, or other type of bed cushion may cause the patient to experience bed sores or problems with circulation unless the patient is rolled over frequently. The human bed 91 may effectively eliminate the problems commonly associated with standard mattresses or waterbeds, in that the saturated foam core allows the body weight of the individual to be more evenly distributed, preventing continuous pressure from being exerted on the body's "pressure points", or points of contact with the bed or liner, which leads to bed sores and other circulation problems.

Similar to the bed liner 90, the human bed 91 consists of a foam core (not shown), surrounded by a vinyl covering 94, having upper 96 and lower (not shown) sheets fused together, as described with reference to the pet bed 70 above. Also similar to the bed liner 90 and pet bed 70, the human bed 91 has a simple liquid inlet and outlet 98 for introduction and removal of liquid into and out of the human bed 91. The liquid inlet and outlet 98 is attached in a water tight fashion to the vinyl covering 94 and the foam core is saturated with water as the preferred liquid.

The human bed 91 is normally at room temperature unless the bed 91 had been recently used. The bed 91 can be made cooler by adding cooler liquid to the bed 91. In the bed 91, the thermal regulating unit 92, when activated via controls thereon, provides a way to cool or heat the liquid within the bed 91 depending on the settings of the unit 92. To accomplish cooling or heating the liquid, a liquid transfer tube 100 is connected to the bed 91. A pump mechanism (not shown) will cause liquid within the bed 91 to enter the tube 100 and be directed toward the unit 92, as illustrated by arrow 102. The unit 92 then cools or heats the liquid and directs the liquid back into the human bed 91, as illustrated by arrow 104, for circulation therein.

Referring next to FIG. 10, a top perspective view of another embodiment of the insert for use as a substantially encapsulating thermal regulating device 110 to control the body temperature of the user, for example, as specified by a physician or for hospital use, is illustrated. This alternative embodiment is contemplated for use in caring for trauma or burn victims, for example. Typically, when medical personnel must cool the body temperature of a burn or other trauma victim, the victim must be physically wrapped in cold, wet sheets and covered with large amounts of ice. The ice must be periodically replenished in order to maintain a chilling environment for the victim. The encapsulating bed 110 of the present invention provides an alternative to this method.

The encapsulating device 110 is similar to the previously described human bed 91 except that the encapsulating device 110 has a receiving area 114 within for receiving a body 116. An aperture 118 formed in the encapsulating device 110 receives the head 120 of the body 116. In accordance with one embodiment, bed 110 forms a burn or trauma treatment encasing device to thermally regulate the victim's temperature while providing a non-stick support for the transport of the patient. The bed 110 can be stored, without temperature regulator, in its "dry" condition within an emergency vehicle such as a flight for life helicopter where space is at a premium.

The encapsulating device 110 consists of a foam core (not shown) preferably constructed from a reticulated foam. The foam core is saturated with liquid and snugly enclosed by a vinyl covering 112. Both the foam core and vinyl covering 112 completely surround the body 116 to provide maximum thermal control benefit for the body 116. The encapsulating bed 110, similar to the human bed 90, has a simple liquid inlet and outlet (not shown) for introduction and removal of liquid into and out of the encapsulating bed 110. The liquid inlet and outlet is attached in a water tight fashion to the vinyl covering 112. The foam core is saturated with water as the preferred liquid.

Preferably, the encapsulating bed 110 has a dimension larger than the body size of a human to allow a human to comfortably enter the encapsulating bed 110. Of course, having the size of the encapsulating bed 110 being substantially larger than the size of the human's body size provides additional volume and surface area to dissipate the human's body heat.

In the encapsulating bed 110, a thermal regulating unit 122, when activated via controls thereon, provides a way to cool or heat the liquid within the encapsulating bed 110 depending on the settings of the unit 122. To accomplish cooling or heating the liquid, a liquid transfer tube 124 is connected to the encapsulating bed 110. A pump mechanism (not shown) will cause liquid within the bed 110 to enter the tube 124. The unit 122 then cools or heats the liquid in a conventional manner and directs the liquid back into the encapsulating bed 110 for circulation therein.

As noted above, since the encapsulating bed 110 is contemplated for use with serious trauma victims, such as burn patients, it is preferred that the vinyl covering 112 in the receiving area 114 be covered with a non-stick substance, for instance TEFLON® brand non-stick coating, so that the patient can be easily inserted into and removed from the receiving area 114 with a minimum of discomfort. Likewise, when caring for burn victims or other serious trauma patients, it is desirable to avoid prolonged or continuous pressure on the victim's injuries and to avoid frequent movement of the patient. As described above with reference to the human bed 91, the structure of the encapsulating device 110, specifically, the saturated form core, avoids problems such as bed sores or circulatory conditions associated with standard mattresses and waterbeds by more evenly distributing the patient's weight across the bed's surface and providing more cushion and "give" on the body's pressure points and injuries.

Figure 11:
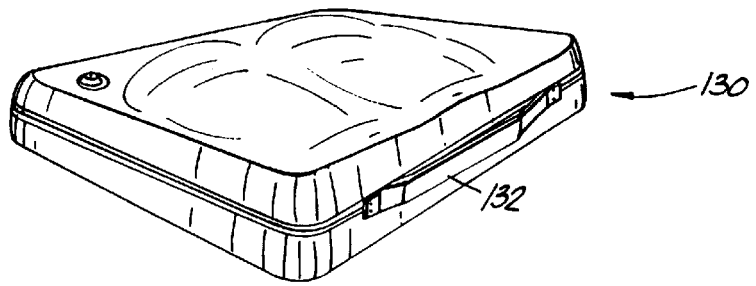
FIG. 11 is a top perspective view of yet still another alternative embodiment of the liquid container of the present invention for use as a seat cushion.

Referring next to FIG. 11, a top perspective view of a further alternative embodiment of the insert for use as a seat cushion 130 is illustrated. The seat cushion 130 of the present invention is substantially similar to the pet bed 70. The seat cushion 130 further comprises a handle 132 providing an easier carrying method when desired.

Referring next to FIGS. 12 and 13, a further embodiment of the instant invention for use as a lounge chair liner 140 is illustrated. The lounge chair liner 140 of the present invention is substantially similar to the pet bed 70 and the seat cushion 130. The lounge chair liner 140 further comprises a plurality of insert sections 132, 134, 136 to better control and regulate the temperature of the person using the lounge chair 138. Each section 132, 134, 136 can be attached to each adjoining section or the sections 132, 134, 136 may be free from connections to an adjoining section.

It will be realized by those skilled in the art that the more "closed" the cellular structure of the foam, the more mechanical support provided by the liquid saturated foam filled device. However, the more closed the cell structure, the less mobility of the liquid within the foam, hence, the less mixing of the liquid contained within the foam. It will also be realized that the liquid must permeate substantially all the cells of the foam to be effective in accordance with this invention. It will further be realized that the liquid can be selected such that certain heat capacity characteristics are imbued to the device as a whole.

Applicants' present invention utilizes the relationship between the sealed envelope or liquid impervious outer membrane and the liquid-saturated foam core to provide the novel support with the circulability of the liquid within the core obviating the need for multiple chambers and any restrictive valving system between such chambers. Therefore, unlike previous unsuccessful devices, the foam of the present invention allows circulability of the liquid-like material within the confines of the single device, while the liquid saturation provides stability and support for the user. There is no requirement of complex valving devices disposed in a membrane to move liquid back and forth between sealed compartments.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A thermal regulating cushioning device comprising:
    a flexible, deformable outer membrane being adapted to sealably receive a liquid material therein;
    a foam core being encased, within and in intimate contact with, but not bonded to, said flexible, deformable outer membrane wherein said foam core has a dimension substantially coincident with said outer membrane;
    a liquid material being sealably contained within said flexible, deformable outer membrane and saturating said foam core, said liquid material being at least partially circulatable through said foam core wherein the cooperation of said saturated foam core and said sealable flexible membrane provide a substantially uniform, thermal regulating medium and structural support such that said cushioning device is readily, uniformly deformable when a load is applied thereto.

2. The thermal regulating cushioning device of claim 1 wherein said foam core further comprises reticulated polyurethane foam having a porosity ranging from 10 pores per inch to 60 pores per inch.

3. The thermal regulating cushioning device of claim 1 wherein the outer membrane of said fluid container further comprises vinyl having a thickness ranging from one millimeter to two hundred millimeters.

4. The thermal regulating cushioning device of claim 1 and further comprising a resealable inlet and outlet valve for ingress and egress of said liquid material.

5. The thermal regulating cushioning device of claim 1 wherein said flexible outer deformable membrane further comprises a lower outer membrane having a non-sliding surface functioning to hold said device in a predetermined position.

6. The thermal regulating cushioning device of claim 5 wherein said nonsliding surface is a studded cloth chosen from a group consisting of rubber studded cloth and vinyl studded cloth.

7. A thermal regulating cushioning device comprising:
    a plurality of segments of consistent size, each of said segments connectable to at least one other segment, whereby the length of said device is selectively variable, each of said segments comprising:
        a flexible, deformable outer membrane being adapted to sealably receive a liquid material therein;
        a foam core being encased within and in intimate contact with, but not bonded to, said flexible, deformable outer membrane wherein said foam core has a dimension substantially coincident with said outer membrane;
        a liquid material being sealably contained within said flexible, deformable outer membrane and saturating said foam core, said liquid material being at least partially circulatable through said foam core wherein the cooperation of said saturated foam core and said sealable flexible membrane provide a substantially uniform, thermal regulating medium and structural support such that said cushioning device is readily, uniformly deformable when a load is applied thereto.

8. A method of regulating the temperature of a user in intimate contact with a cushioning device having a foam core saturated with a liquid material, said foam core encased within and in intimate contact with, but not bonded to a deformable, sealable flexible membrane and having a dimension substantially coincident with said outer membrane, wherein said liquid material is at least partially circulatable through said foam core wherein the cooperation of said saturated foam core and said sealable flexible membrane provide a substantially uniform, thermal regulating medium and structural support for said user, and wherein said cushioning device is readily, uniformly deformable when a load is applied thereto.

9. The method for regulating the temperature of a user of claim 8 wherein said flexible outer membrane has a non-sticking surface.

* * * * *